US008877447B2

(12) United States Patent
Janssen-Heininger et al.

(10) Patent No.: US 8,877,447 B2
(45) Date of Patent: Nov. 4, 2014

(54) DETECTION OF GLUTATHIONYLATED PROTEINS

(75) Inventors: Yvonne M. Janssen-Heininger, Charlotte, VT (US); Niki Reynaert, Maasmechelen (BE)

(73) Assignees: The University of Vermont and State Agriculture College, Burlington, VT (US); Universiteit Maastricht, Maastricht (NL)

( * ) Notice: Subject to any disclaimer, the term of this patent is extended or adjusted under 35 U.S.C. 154(b) by 1858 days.

(21) Appl. No.: 11/698,300

(22) Filed: Jan. 25, 2007

(65) Prior Publication Data

US 2008/0014595 A1    Jan. 17, 2008

Related U.S. Application Data

(60) Provisional application No. 60/761,956, filed on Jan. 25, 2006, provisional application No. 60/774,060, filed on Feb. 16, 2006.

(51) Int. Cl.
  *G01N 33/53*   (2006.01)
  *G01N 33/68*   (2006.01)
  *G01N 33/58*   (2006.01)

(52) U.S. Cl.
  CPC ...... *G01N 33/6893* (2013.01); *G01N 2800/122* (2013.01); *G01N 2800/24* (2013.01); *G01N 33/6842* (2013.01); *G01N 33/58* (2013.01)
  USPC ........................................ 435/7.1

(58) Field of Classification Search
  None
  See application file for complete search history.

(56) References Cited

U.S. PATENT DOCUMENTS

| 6,379,664 | B1 | 4/2002 | Lou et al. |
| 6,806,057 | B2 | 10/2004 | Snyder et al. |
| 7,001,738 | B2 | 2/2006 | Snyder et al. |
| 2005/0026227 | A1 | 2/2005 | Snyder et al. |
| 2005/0238734 | A1* | 10/2005 | Janssen et al. ............. 424/718 |

FOREIGN PATENT DOCUMENTS

| WO | WO 2005/10101 A | 10/2005 |
| WO | WO 2008/154012 | 12/2008 |

OTHER PUBLICATIONS

Giustarini et al., "S-glutathionylation: from redox regulation of protein functions to human diseases", *J. of Cellular and Molecular Medicine*, vol. 8, No. 2, (Apr. 2004) 201-212.
Search report from International Application No. PCT/US2007/001931, mailed Feb. 4, 2008.
Written Opinion from International Application No. PCT/US2007/001931, mailed Feb. 4, 2008.
Reynaert, et al., "Dynamic Redox Control of NF" Proceedings of the National Academy of Sciences of the United States of America (2006), vol. 103:, pp. 13086-13091.
Reynaert, et al., "Modulation of Glutaredoxin-1 Expression in a Mouse Model of Allergic Airway Disease"Am J Respir Cell Mol Biol, vol. 36, pub. Feb. 2007, pp. 148-151.
Berlett, B. et al., "Protein Oxidation in Aging, Disease, and Oxidative Stress," *Journal of Biological Chemistry* 1997 272 33(20313-20316).
Bishop, C. et al., "A Pilot Study of the Effect of Inhaled Buffered Reduced Glutathione on the Clinical Status of Patients with Cystic Fibrosis," www.chestjournal.org, 2005 127 1 (308-317).
Cheng, G. et al., "Detection of S-glutathionylated proteins by glutathione S-transferase overlay," *Archives of Biochemistry and Biophysics* 2005 435(42-49).
Finkel, T., "Oxidant signals and oxidative stress," *Current Opinion in Cell Biology* 2003 15(247-254).
Reynaert, N. et al., "In situ detection of S-glutathionylated proteins following glutaredoxin-1 catalyzed cysteine derivatization," *Biochimica at Biophysica Acta* 2006 1760(380-387).
Schulz, J. et al., "Glutathione, oxidative stress and neurodegeneration," *Eur. J. Biochem.* 2000 267(4904-4911).

(Continued)

*Primary Examiner* — Lisa J Hobbs
(74) *Attorney, Agent, or Firm* — Wolf, Greenfield & Sacks, P.C.

(57) ABSTRACT

The present invention, in some aspects, relates to systems and methods for determining oxidized proteins, including glutathionylated proteins such as S-glutathionylated proteins. The systems and methods of the invention can be used in vitro (e.g., in cell or tissue culture) or in vivo, for example, to diagnose a person having an oxidative stress condition. For instance, in some cases, the invention can be used to spatially determine the location and/or concentration of oxidized proteins within cells and/or tissues (e.g., through visual detection). In one set of embodiments, a glutathionylated or otherwise oxidized moiety on a protein may be reacted with a detection entity, which may be, for example, fluorescent, radioactive, electron-dense, able to bind to a signaling entity or a binding partner in order to produce a signal, etc. As a specific example, a glutathionylated moiety on a glutathionylated protein may be reacted with an alkylating agent to form an alkylthio moiety; the alkylthio moiety may include a detection entity or otherwise be able to interact with a signaling entity. In some embodiments, other moieties on the protein may be altered or blocked before reaction of the protein with the detection entity. Such moieties on the protein may be, for instance, non-oxidized or non-glutathionylated moieties able to react with the detection entity. As a particular example, in a protein containing a glutathionylated moiety and non-glutathionylated thiol moieties, the thiol moieties may first be altered or blocked prior to reaction of the protein with the detection entity. Also provided in certain aspects of the present invention are kits for determining oxidized proteins, which may include components such as detection entities, alkylating agents, blocking agents, reducing agents, signaling entities, binding partners, antibodies, instructions, and the like.

7 Claims, 7 Drawing Sheets

(56) References Cited

OTHER PUBLICATIONS

Anathy Vikas et al., "Redox amplification of apoptosis by caspase-dependent cleavage of glutaredoxin 1 and S-glutathionylation of Fas" The Journal of Cell Biology, vol. 184(2), 241-252.

Chivers et al., "The CXXC Motif: A Rheostat in the Active Site," 1997, Biochemistry 36: 4061-4060.

Erlendsson et al., "*Bacillus subtilis* ResA is a Thiol-Disulfide Oxidoreductase involved in Cytochrome c Synthesis," JBC 278: 17852-17858.

Fernando M. Rohan et al., "Mitochondrial thioltransferase (glutaredoxin 2) has GSH-dependent and thioredoxin reductase-dependent peroxidase activities in vitro and in lens epithelial cells," The FASEB Journal: Official Publication of the Federation of American Societies for Experimental Biology, vol. 20(4), Dec. 2006, 2645-2647.

Johansson et al., "Human Mitochondrial Glutaredoxin Reduces S-Glutathionylated Proteins with High Affinity Accepting Electrons from Either Glutathione or Thioredoxin Reductase," 2004, JBC 279: 7537-7543.

Sagemark Johan et al., "Redox properties and evolution of human glutaredoxins," Proteins Structure Function and Bioinformatics, vol. 68(4), Jun. 2007, 879-892.

Timmer J C et al., "Caspase substrates" Cell Death and Differentiation, vol. 14(1), Jan. 2007, 66-72.

Watson et al., "Thioredoxin and Its Role in Toxicology" 2004, Toxicological Sci. 78: 3-14.

Argyrou, A. et al., "Flavoprotein Disulfide Reductases: Advances in Chemistry and Function," *Progress in Nucleic Acid Research and Molecular Biology*, 2004, 78, 89-141.

Pan, S. et al., "Glutathiolation Regulates Tumor Necrosis Factor-α-Induced Caspase-3 Cleavage and Apoptosis," *Circulation Research*, 2007, 213-219.

\* cited by examiner c10 CELLS c10 CELLS c10 CELLS c10 CELLS

C57BL/6

C57BL/6

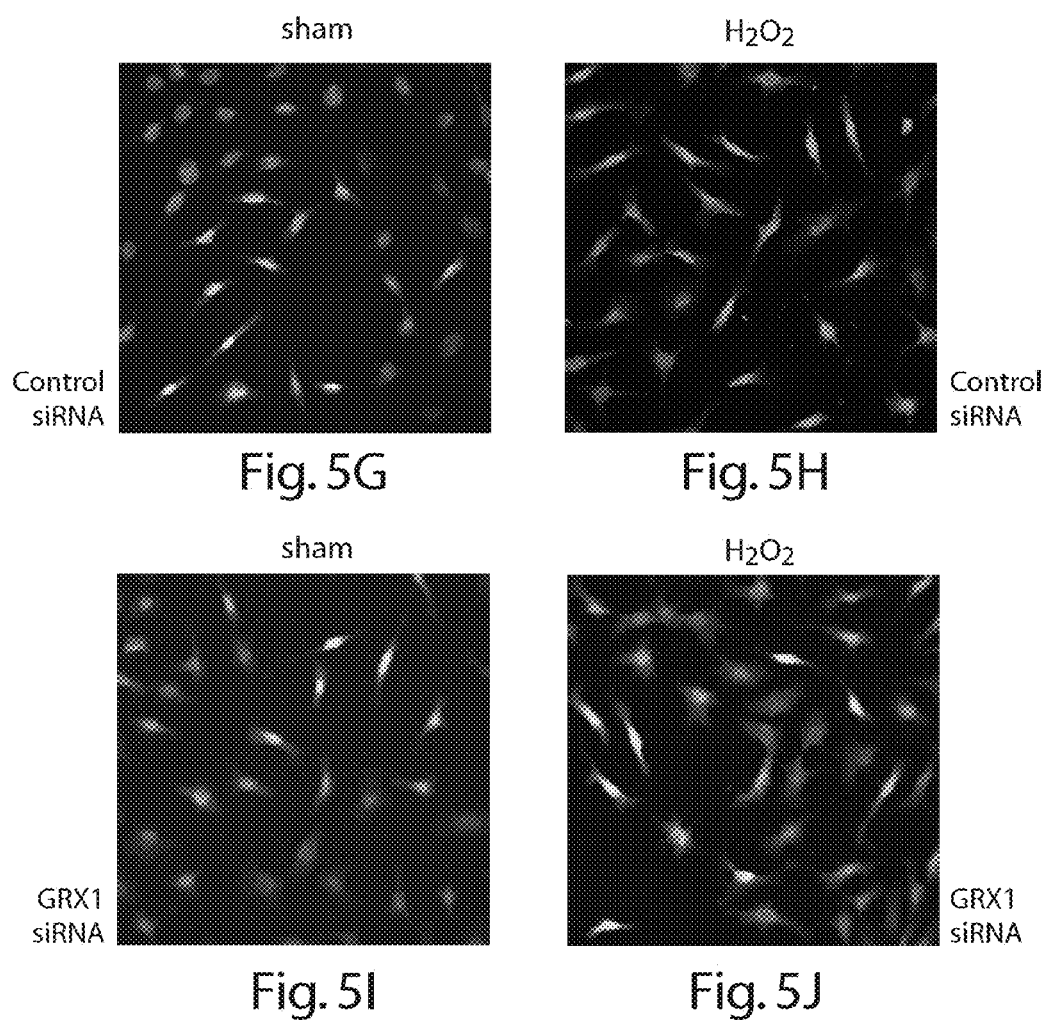

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
catggctcag gagtttgtga                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 2
gccacccctt ttataactgc                                               20

<210> SEQ ID NO 3
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 3
ccggatccat gtacccatac acgtcccaga ctacgctgct caggagtttt gtgaactg     58

<210> SEQ ID NO 4
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 4
gccacccctt ttataactgc gaattccgg                                     29
```

US 8,877,447 B2

DETECTION OF GLUTATHIONYLATED PROTEINS

RELATED APPLICATIONS

This application claims the benefit of U.S. Provisional Patent Application Ser. No. 60/761,956, filed Jan. 25, 2006, entitled "Detection of Glutathionylated Proteins," by Y. Janssen-Heininger; and U.S. Provisional Patent Application Ser. No. 60/774,060, filed Feb. 16, 2006, entitled "Detection of Glutathionylated Proteins," by Y. Janssen-Heininger. Each of these is incorporated herein by reference.

GOVERNMENT FUNDING

Research leading to various aspects of the present invention were sponsored, at least in part, by NIH RO1 HL60014, HL60812, Public Health Service P20 RL15557 (NCRR COBRE) and PO1 HL67004. The U.S. Government has certain rights in the invention.

FIELD OF INVENTION

The present invention generally relates to systems and methods for determining oxidized proteins, and in particular, to systems and methods for determining glutathionylated proteins. In some cases, the present invention relates to visualization techniques for determining the spatial locations and/or concentrations of glutathionylated or otherwise oxidized proteins within cells and/or tissues. In certain embodiments, the present invention relates to methods of diagnosing subjects having oxidative stress conditions.

BACKGROUND

The tripeptide glutathione (2-amino-5-{[2-[(carboxymethyl)amino]-1-(mercaptomethyl)-2-oxoethyl]amino}-5-oxopentanoic acid, or γ-glutamylcysteinylglycine) is considered one of the major anti-oxidants of the human body, with cellular concentrations in the millimolar range. A number of enzyme systems exist that are dedicated to maintaining glutathione homeostasis, including the rate-limiting enzyme for its synthesis, γ (gamma)-glutamylcysteine synthetase, and glutathione reductase, which reduces GSSG, using NADPH as a cofactor. Glutathione may serve a major role in maintaining the reduced state of cellular protein thiol groups. It can accomplish this role through the function of glutathione peroxidases, which utilize GSH to reduce hydroperoxides. In addition, upon oxidative stress, glutathione often spontaneously forms mixed disulfides with protein thiol groups, causing reversible S-glutathionylation.

S-glutathionylation of thiols may confer protection against their irreversible oxidation, like for instance the formation of sulphonic acid moieties. If the targeted cysteine is a functionally critical amino acid, S-glutathionylation may also modify protein function. For instance S-glutathionylation of the p50 subunit of NF-κB (NF-kappaB) as well as of the c-Jun subunit of AP-1 may be linked to repression of DNA binding activity of these transcription factors. The activities of protein kinase C, glyceraldehyde-3-phosphate dehydrogenase, and HIV-1 protease may also be adversely affected by S-glutathionylation.

Mammalian glutaredoxins (GRX), or thioltransferases, are members of the thiol-disulfide oxidoreductase family. They are often characterized by a thioredoxin fold and a Cys-Pro-Tyr(Phe)-Cys active site. Examples include GRX1, a cytosolic protein, and GRX2, which may be directed to the mitochondria by a mitochondrial leader sequence and/or can also occur in the nucleus following alternative splicing. Mammalian glutaredoxins may specifically catalyze the reversible reduction of protein-glutathionyl-mixed disulfides to free sulfhydryl groups, using GSH as a cofactor. GRXs through their deglutathionylation activity could therefore play a unique role in redox signaling.

SUMMARY OF THE INVENTION

The present invention generally relates to systems and methods for determining oxidized proteins, such as glutathionylated proteins. In some cases, the present invention relates to visualization techniques for spatially determining the spatial locations and/or concentrations of glutathionylated or otherwise oxidized proteins within cells and/or tissues. The subject matter of the present invention involves, in some cases, interrelated products, alternative solutions to a particular problem, and/or a plurality of different uses of one or more systems and/or articles.

One aspect of the invention provides a diagnostic method. In one set of embodiments, the diagnostic method comprises providing a sample taken from a subject; exposing the sample to an alkylating agent able to react a first thiol moiety on a protein to produce an alkylthio moiety; and exposing the sample to a reducing agent able to react a glutathionylated moiety on the protein to produce a second thiol moiety. The method also includes diagnosing the subject with an oxidative stress condition based on a result of the assay, in certain embodiments.

Another aspect of the invention provides a method for determining a glutathionylated protein. The method, in one set of embodiments, includes the steps of reacting a first thiol moiety on a protein to form an alkylthio moiety, reacting a glutathionylated moiety on the protein to form a second thiol moiety, and reacting the second thiol moiety with an alkylating agent comprising a detection entity to form a second alkylthio moiety to determine protein glutathionylated.

In another set of embodiments, the method is defined, at least in part, by a step of reacting a glutathionylated moiety on a protein to form an alkylthio moiety. In yet another set of embodiments, the method includes the steps of reacting a first thiol moiety on a protein to form an alkylthio moiety, and reacting a glutathionylated moiety on the protein to form a second thiol moiety.

In one set of embodiments, the method comprises a step of spatially determining a glutathionylated protein in tissue. In still another set of embodiments, the method includes a step of non-reversibly reacting a glutathionylated moiety on a protein with a detection entity.

In yet another set of embodiments, the method includes acts of determining a glutathionylated state of a protein within a subject, and diagnosing the subject with a medical condition based on the glutathionylated state of the protein.

A kit is provided in another aspect of the invention. In certain embodiments, the kit includes a container housing an alkylating agent and a reducing agent. In some cases, the alkylating agent is able to react a first thiol moiety on a protein to an alkylthio moiety, and the reducing agent is able to react a glutathionylated moiety on the protein to a second thiol moiety.

In another aspect, the present invention is directed to a method of promoting one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 5A-5J illustrate the manipulation of GRX1 expression, in yet another embodiment of the invention.

BRIEF DESCRIPTION OF THE SEQUENCES

Figure 1A:
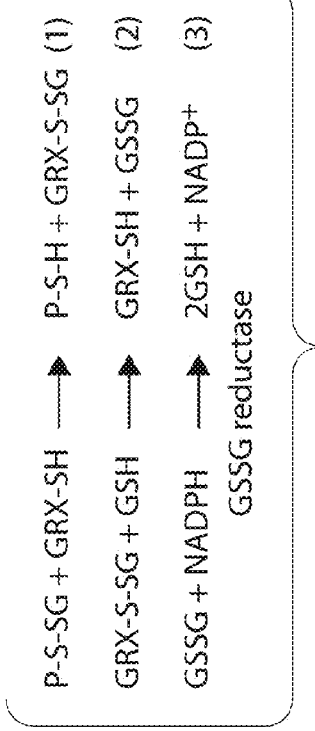
FIGS. 1A and 1B are schematic diagrams for determining glutathionylated proteins according to one embodiment of the invention.

SEQ ID NO: 1 is CATGGCTCAGGAGTTTGTGA, a primer sequence;

SEQ ID NO: 2 is GCCACCCCTTTTATAACTGC, a primer sequence;

SEQ ID NO: 3 is CCGGATCCATGTACCCATACACGTCCCAGACTACGCTGCTCAGGAGTTTTGTGAACTG, a primer sequence; and SEQ ID NO: 4 is GCCACCCCTTTTATAACTGCGAATTCCGG, a primer sequence.

DETAILED DESCRIPTION

The present invention, in some aspects, relates to systems and methods for determining oxidized proteins, including glutathionylated proteins such as S-glutathionylated proteins. The systems and methods of the invention can be used in vitro (e.g., in cell or tissue culture) or in vivo, for example, to diagnose a subject as having an oxidative stress condition. For instance, in some cases, the invention can be used to spatially determine the location and/or concentration of oxidized proteins within cells and/or tissues (e.g., through visual detection). In one set of embodiments, a glutathionylated or otherwise oxidized moiety on a protein may be reacted with a detection entity, which may be, for example, fluorescent, radioactive, electron-dense, able to bind to a signaling entity or a binding partner in order to produce a signal, etc. As a specific example, a glutathionylated moiety on a glutathionylated protein may be reacted with an alkylating agent to form an alkylthio moiety; the alkylthio moiety may include a detection entity or otherwise be able to interact with a signaling entity. In some embodiments, other moieties on the protein may be altered or blocked before reaction of the protein with the detection entity. Such moieties on the protein may be, for instance, non-oxidized or non-glutathionylated moieties able to react with the detection entity. As a particular example, in a protein containing a glutathionylated moiety and non-glutathionylated thiol moieties, the thiol moieties may first be altered or blocked prior to reaction of the protein with the detection entity. Also provided in certain aspects of the present invention are kits for determining oxidized proteins, which may include components such as detection entities, alkylating agents, blocking agents, reducing agents, signaling entities, binding partners, antibodies, instructions, and the like.

Various aspects of the present invention relate to systems and methods for determining oxidized proteins, including glutathionylated proteins such as S-glutathionylated proteins. In some aspects, the present invention relates to visualization techniques for spatially determining the spatial locations and/or concentrations of glutathionylated or otherwise oxidized proteins within cells and/or tissues. An "oxidized" protein, as used herein, is a protein in which at least one (native) amino acid residue of the protein has been oxidized in some fashion. As an example, glutathione may react with a residue on the protein to glutathionylate the residue. Thus, as used herein, a "glutathionylated" protein is a protein in which at least one amino acid residue of the protein has been glutathionylated, i.e., the amino acid residue has reacted with gluatathione, typically through the addition of the gluatathione (or a portion thereof) to the residue. Residues that may undergo reactions with glutathione include sulfhydryl moieties (—SH) (e.g., from a cysteine residue), hydroxyl moieties (—OH) (e.g., from a serine residue or a threonine residue), or the like. As a particular example, if the residue includes a sulfhydryl moiety (—SH) (also referred to as a thiol moiety), reaction of the moiety with glutathione can produce a S-glutathionylated moiety, i.e., —S—S-G, where "G" represents the glutathione tripeptide). The "S—" signifies reaction with the sulfhydryl moiety.

It should be understood that, in the following descriptions, although the determination of oxidized proteins is often described in terms of the determination of S-glutathionylated proteins, this is by way of example only, and the determination of other types of oxidized proteins and/or glutathionylated proteins is also within the scope of the invention. As used herein, "determining" refers to the detection and/or analysis of an entity, either quantitatively or qualitatively. Determination of an entity may include determination of the presence or absence of the entity, and/or a measurement of the amount or degree of the entity, e.g., the concentration of the entity, the density of the entity, etc. In some cases, the location of an entity may be determined, for example, the location of the entity within a cell, within a tissue, etc.

According to one aspect, an oxidized protein can be determined by attaching a detection entity to an oxidized residue on the protein, for example, the protein may be spatially or visually determined. As used herein, a "detection entity" is an entity that can be determined in some fashion, either directly or indirectly. For instance, the detection entity may be fluorescent, radioactive, electron-dense, a member of a binding pair, a substrate for an enzymatic reaction, an antigen for an antibody, etc. In some cases, the detection entity itself is not directly determined, but instead interacts with a second entity (a "signaling entity") in order to effect determination; for example, coupling of the signaling entity to the detection entity may result in a determinable signal. As examples, the detection entity and the signaling entity may each include one member of a binding pair, for example, nucleic acid/nucleic acid, nucleic acid/protein, protein/protein, antibody/antigen, antibody/hapten, enzyme/substrate, enzyme/inhibitor, enzyme/cofactor, receptor/hormone, receptor/effector, ligand/cell surface receptor, virus/ligand, etc. The term "binding partner," as used herein, refers to a molecule that can undergo binding with a particular molecule, forming a "binding pair." Thus, as an example, the detection entity may include a biotin moiety and the signaling entity may include an avidin or a streptavidin moiety that is determinable in some fashion, for example, by being coupled to a radioactive, a fluorescent moiety, an electron-dense moiety, etc. As another example, the signaling entity may be an antibody able to recognize the detection entity on the protein. The antibody may be labeled in some way, for example, radioactively, fluorescently, using an electron-dense moiety, etc.

In some embodiments, the detection entity may be added to the oxidized residue using an alkylating agent, for example, directly by reacting the oxidized residue directly with an alkylating agent, indirectly by reducing the oxidized residue and thereafter reacting the reduced residue with an alkylating agent, etc. As used herein, an "alkylating agent" is an agent able to alkylate a target reactant, i.e., the agent interacts with the target reactant such that an alkyl moiety is added to the target reactant (i.e., the compound becomes "alkylated"). In some cases, the alkylating agent itself may include the alkyl moiety that is transferred to the target reactant, e.g., the alkylating agent causes the formation of a covalent bond between the alkyl moiety and the target reactant. Typically, when the target reactant is a protein, the alkylating agent is able to react with the protein to cause alkylation of at least one moiety on the protein, in some cases without denaturing or otherwise damaging the protein. As one particular example, the alkylating agent may alkylate a thiol (—SH) moiety on a protein (e.g., from a cysteine residue) to form an alkylthio (—SR) moiety, where R is an alkyl moiety and "-" indicates attachment to the protein. It is to be noted that an alkylthio moiety does not include a disulfide (—SSR) moiety. As another example, the alkylating agent may alkylate a hydroxy (—OH) moiety on the protein (e.g., from a serine residue or threonine residue) to form an alkoxy (—OR) moiety. In some cases, in order to prevent or reduce signal interference with non-oxidized residues on the protein and/or from other, non-oxidized proteins, a blocking reaction is provided by the invention, where the non-oxidized residues are blocked or inhibited in some fashion, prior to the attachment of the detection entity on the oxidized residues.

As used herein, an "alkyl" moiety, attached to a residue, is a moiety containing at least one carbon atom that is covalently bound to the residue, and may include any number of carbon atoms, for example, between and 1 and 25 carbon atoms, between 1 and 20 carbon atoms, between 1 and 15 carbon atoms, between 1 and 10 carbon atoms, or between 1 and 5 carbon atoms. In some embodiments, the alkyl moiety will contain at least 1 carbon atom, at least 3 carbon atoms, at least 5 carbon atoms, or at least 10 carbon atoms; in other embodiments, the alkyl moiety will have at most 10 carbon atoms, at most 5 carbon atoms, or at most 3 carbon atoms. The alkyl moiety may be a non-cyclic or a cyclic moiety. The carbon atoms within the alkyl moiety may be arranged in any configuration within the alkyl moiety, for example, as a straight chain (i.e., a n-alkyl such as methyl, ethyl, propyl, butyl, pentyl, hexyl, heptyl, octyl, etc.), a branched chain, i.e., a chain where there is at least one carbon atom covalently bonded to at least three carbon atoms (e.g., a t-butyl moiety, an isoalkyl moiety such as an isopropyl moiety or an isobutyl moiety, etc.), a ring structure (e.g., cyclopropyl, cyclobutyl, cyclopentyl), etc. or any combination thereof. The alkyl moiety may contain only single bonds, or may contain one or more double and/or triple bonds within its structure, for example, as in an alkene, an alkyne, an alkadiene, an alkadiyne, an alkenyne, etc. In some cases, the alkyl moiety contains only carbon and hydrogen atoms; however, in other embodiments, the alkyl moiety may also contain one or more substituents, i.e., a non-carbon, non-hydrogen moiety may be present within the alkyl moiety, e.g., the alkyl moiety may be "heterogeneous," as in a heterocycloalkyl moiety. In certain embodiments, the alkyl moiety can include a halogen such as chlorine or bromine, an alkoxy moiety, an amine moiety, a carbonyl, a hydroxide, etc. If more than substituent is present within the alkyl moiety, then the substituents may each independently be the same or different.

In one set of embodiments, a glutathionylated protein is determined by reacting a glutathionylated moiety on the protein to form an alkylthio moiety, for example, spatially determined (e.g., through visualization). In some cases, the alkylthio moiety may include a detection entity. An example of such a reaction is the initial reduction of a glutathionylated moiety on the protein to a thiol moiety, followed by alkylation of the thiol moiety to form an alkylthio moiety. Any suitable reaction able to convert the glutathionylated moiety on the protein to a thiol moiety may be used, for example, reduction of the glutathionylated moiety. In one embodiment, the glutathionylated moiety is reduced by exposing the protein to a reducing agent. A "reducing agent," as used herein, is given its ordinary meaning in the art, i.e., an agent that is able to cause a reactant to attain a more negative oxidation state. An example of a reducing agent of a glutathionylated moiety is a glutaredoxin, which catalyzes the reduction of the moiety to a thiol moiety. Non-limiting examples of glutaredoxin include GRX1 (GLRX) and GRX2 (GLRX2) in mammals. Other examples of reducing agents include, but are not limited to, an ascorbate (for example, sodium ascorbate or potassium ascorbate), dithiothreitol (DTT), glutathione (GSH), NADPH, NADH, beta-mercaptoethanol, tris-(2-carboxyethyl)phosphine, tris-(2-cyanoethyl)phosphine, etc.

The thiol moiety (—SH) may then be reacted to produce an alkylthio moiety (—SR), which may include a detection entity in some cases, for example, a binding partner such as biotin or avidin, a fluorescent moiety, a radioactive moiety, or the like. As an example, the thiol moiety may be exposed to an alkylating agent able to react with the thiol moiety to form an alkylthio moiety. For example, in one embodiment, the alkylating agent can include a maleimide moiety. In some cases, the maleimide may be covalently bonded to a detection entity, for example, a biotin moiety or a fluorescent moiety. As a specific non-limiting example, the alkylating agent may be N-(3-maleimidylpropionyl)biocytin (MBP) (or N-[6-(biotinamido)hexyl]-3-(2-pyridyldithio)propionamide), and/or a derivative thereof. As used herein, a "maleimide moiety" is a moiety having a general maleimide structure, e.g.:

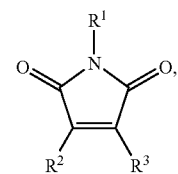

where each of $R^1$, $R^2$, and $R^3$ independently is a hydrogen atom (i.e., maleimide) or represents other, non-hydrogen atoms or group of atoms, for example, halogens, alkyls, alkoxyls, etc. In some cases, at least one of $R^1$, $R^2$, and $R^3$ may indicate attachment of the maleimide moiety to a fluorescent moiety, a biotin moiety (e.g., as in MBP), etc. Additionally, as used herein, a "biotin moiety" is a moiety having a general biotin structure, e.g.:

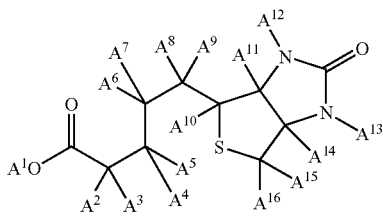

where each A in the above structure independently is a hydrogen atom (i.e., biotin) or represents other, non-hydrogen atoms or group of atoms, for example, halogens, alkyls, alkoxyls, etc. In some cases, at least one A in the above structure may indicate attachment of the biotin moiety to other moieties, for example, a fluorescent moiety.

In another embodiment, the alkylating agent includes an iodoacetamide moiety or an iodoacetate moiety, for example, as in 2-iodoacetamide or 2-iodoacetate, respectfully. In yet another embodiment, the alkylating agent includes at least one of p-chloromercuriphenylsulfonate, p-chloromercuribenzoate, dithiobis(2-nitro)benzoic acid, N-tosyllysyl chloromethyl ketone, 6-acryloyl-2-dimethylaminonaphthalene, dansyl aziridine, acrylodan, a benzylic halide, or a bromomethylketone. In some embodiments, more than one alkylating agent may be present, for example, N-ethylmaleimide and 2-iodoacetamide or 2-iodoacetate, etc.

In some cases, when other, unmodified thiol moieties are present within the protein and/or within other, proximate proteins near the protein suspected of being glutathionylated (or otherwise oxidized), the unmodified (i.e., non-glutathionylated) thiol moieties may be initially blocked or otherwise altered before the glutathionylated moiety is converted into an alkylthio moiety, such that the unmodified thiol moieties are not able to react in the same fashion as the glutathionylated moieties, which may confound the determination and analysis of the glutathionylated moieties. In other cases, however, some side reactions involving other unmodified thiol moieties on the protein suspected of being glutathionylated and/or other, proximate proteins may be tolerable, as long as determination of glutathionylation within the protein can still be performed, for example, in in vitro assays, in protein studies, through visualization, or the like. Blocking or otherwise altering unmodified thiol moieties may be useful in some embodiments in isolating and/or boosting determination of any glutathionylated moieties on the protein suspected of being glutathionylated, relative to unrelated, unmodified thiol moieties. Any suitable techniques for blocking unmodified thiol groups on a protein from reaction may be used. For example, thiol moieties on the protein may first be converted to alkylthio moieties (which typically will not contain detection entities), prior to reaction of the glutathionylated moieties to form alkylthio moieties containing detection entities. As a non-limiting example, unmodified thiol moieties on a protein may be reacted with N-ethylmaleimide (NEM), methyl methanothiosulfonate, and/or derivatives thereof, prior to reaction/determination of glutathionylated moieties in the protein, for example, using MBP.

In one set of embodiments, the detection entity can be directly determined, e.g., spatially, for example, through the use of fluorescence detection techniques such as spectroscopy, radioactivity, electron microscopy, etc. In other embodiments, however, the detection entity is indirectly determined, for example, through interaction of the detection entity with a signaling entity. For example, the signaling entity and the detection entity may together form a binding pair, e.g., as previously described. Typically, the signaling entity is externally determined, for example, using radioactivity, fluorescence, electron microscopy, etc. As a non-limiting example, if the detection entity comprises a biotin moiety, the signaling entity may include an avidin moiety, a streptavidin moiety, a biotin antibody, etc; the signaling entity may also include a fluorescent moiety, an enzymatic moiety, a radioactive atom, etc. Specific, non-limiting examples include streptavidin horseradish peroxidase (streptavidin-HRP), streptavidin fluorescein, or streptavidin fluorescein isothiocyanate (streptavidin-FITC). In some cases, the detection entity can also be determined as a function of time, for example, by real-time imaging, e.g., via fluorescence, MRI, or the like. As a specific example, a detection entity, such as GSH, may be labeled with a fluorescent entity, and detected in real time via fluorescence microscopy.

The invention, in another aspect, may be used to determine a characteristic of a protein in vivo or in vitro. In one set of embodiments, a protein may be detected in vitro or in isolation, e.g., within a protein assay, for example, within a 96-well plate or other microwell plate. For instance, an embodiment of the invention may be used to determine oxidized proteins such as glutathionylated proteins in a sample, e.g., a synthetically prepared sample, a sample from cell culture or tissue culture, a cell lysate, and/or a sample from a subject, such as a human, a non-human primate, a cow, a horse, a pig, a sheep, a goat, a dog, a cat or a rodent such as a mouse, a rat, a hamster, a guinea pig, etc. A "sample," as used herein, is any cell, body tissue, or body fluid sample obtained from a subject. Examples of body fluids include lymph, saliva, blood, plasma, urine, lung fluid and the like. Samples of tissue and/or cells for use in the various methods described herein can be obtained through standard methods including, but not limited to, tissue biopsy, including punch biopsy and cell scraping, needle biopsy; or collection of blood or other bodily fluids by aspiration or other suitable methods. In some cases, the tissue samples may be frozen, embedded in paraffin, or the like.

In another set of embodiments, oxidized proteins such as glutathionylated proteins may be determined in an intact cell. The intact cell may be alive, or the intact cell may be fixed in some cases. Determination of the protein in the cell may include determining the presence or absence of the proteins within the cell, determining the concentration of the proteins within the cell, and/or determining the location of the proteins within the cell, e.g., within organelles within the cell, such as within the nucleus, within mitochondria, within lysosomes, etc.

The invention, in yet another set of embodiments, provides for the determination of oxidized proteins such as glutathionylated proteins within tissue, for example, brain tissue, lung tissue, etc. In some embodiments, such determination of the glutathionylated and/or other oxidized proteins within the tissue allows the spatial locations and/or concentrations of the proteins within the tissues to be identified and/or measured, for example, quantitatively. The tissue may be alive, or fixed in some cases. Determination of the oxidized proteins may include determining the amount of protein present, and/or determining the spatial location of the oxidized proteins within the tissue, or within portions of the tissue (e.g., within certain structures comprising the tissue, within certain cells within the tissue, within certain regions of cells within the tissue, etc.). Thus, as a non-limiting example, a reaction where glutathionylated proteins become fluorescent may be used, according to the invention, to resolve the location of glutathionylated proteins within a tissue sample, such as within lung tissue.

In still another set of embodiments, the invention provides for the determination of oxidized proteins, such as glutathionylated proteins, within a subject. For example, the invention may be used to diagnose a subject as having an oxidative stress condition, according to one embodiment, e.g., determining the subject with an oxidative stress condition or not, and/or to the degree to which a subject has an oxidative stress condition. Thus, determination of a glutathionylated protein within a subject may used as a biomarker for the oxidative stress condition. In a subject, an oxidative stress condition may be caused by certain types of chronic diseases or conditions, for example, airway inflammation, aging, asthmas, emphysema, cancers, rheumatoid arthritis, atherosclerosis, alcohol addition, certain types of cardiovascular disease, certain types of chronic inflammatory diseases, or certain types of neurodegenerative diseases, such as Lou Gehrig's Disease, Parkinson's Disease, Alzheimer's Disease, sporadic amytrophic lateral sclerosis, or Huntington's Disease. Such diseases are often characterized by chronic altered metabolic states in which there are elevated concentrations of certain reactive oxygen species, such as superoxides, singlet oxygens, peroxynitrite, ozone, or hydrogen peroxide. In some cases, the reactive oxygen species are created by external factors, such as radiation or ultraviolet light. Other agents that may lead to oxidized proteins include, but are not limited to, chemical reagents such as hydrogen peroxide, $NO_x$ species, or the like, or certain types of biological reactions, such as enzymes that produce oxidative intermediate species (e.g., metabolic enzymes). In one embodiment, the oxidative stress condition may be diagnosed within a subject by providing a sample taken from the subject (e.g., a blood sample, cells, fluid, etc.), exposing the sample to a reducing agent, such as an enzyme, able to interact with certain proteins within the sample (e.g., an enzyme or other reducing agent able to react with glutathione or nitroso groups on the protein), and determining if the proteins have been oxidized and in some cases, to what degree. Based on the results of this assay, the subject may be diagnosed as having an oxidative stress condition, which may be indicative of certain diseases, as previously described. Non-limiting examples of suitable reducing agents are described herein, for instance, glutaredoxin. In certain embodiments, blocking reactions may also be used. For instance, prior to exposure of the sample to a reducing agent, the sample may be exposed to an alkylating agent, for instance, to react with non-oxidized thiol moieties.

In some cases, use of an enzyme may offer a high degree of specificity, e.g., with respect to oxidized glutathionylated moieties on the proteins, relative to other, non-glutathionylated moieties on the protein. In some embodiments, such a method may be used to determine whether a subject exhibits an oxidative stress condition, for example, a chronic inflammatory disease, asthma, cancers, or the like, irrespective of the disease or condition that a subject has. Thus, the method can be used for a broad array of diseases or conditions, in contrast to other tests which are often specific to a particular protein or molecule, and thus may miss or incorrectly diagnose, other, similar oxidative stress conditions that a subject may have. In some cases, such a diagnosis may be followed by the prescription and/or administration, to the subject, of a therapeutic intervention, for example, the application of a medicine to treat the subject, etc. In certain embodiments, one or more specific proteins and/or enzymes may be used as biomarkers to determine whether a subject exhibits an oxidative stress condition.

The oxidized protein (e.g., glutathionylated proteins), in some embodiments, may also be spatially determined or resolved within a cell or tissue. For example, an oxidized protein may be determined to be within a cell and/or within a portion of the cell, such as within an organelle, for example, within the nucleus of the cell. In some cases, for instance, certain cells express glutathionylated proteins preferentially within the nucleus, e.g., as further described in the examples, below. In some instances, the concentration and the location of oxidized protein within the cell or tissue may both be determined. For instance, by using fluorescent and/or radioactive signals indicative of oxidized proteins, as previously described, the strength of the respective fluorescent and/or radioactive signal(s) may be correlated with the concentration of oxidized proteins, while the spatial location of the signal(s) may be correlated with the location of the oxidized proteins within the cell/or tissue.

Non-limiting examples of techniques that may be useful in determining oxidized proteins (for instance, oxidized proteins within a cell or a tissue that are reacted with a fluorescent detection entity, and/or a detection entity able to interact with a signaling entity that is or can become fluorescent upon interaction with the detection entity) include fluorescence detection techniques such as spectrofluorimetery, fluorescence microscopy, confocal microscopy, microwell plate readers (for example, for 24-well plates, 96-well plates, 384-well plates, or the like), fluorescence photobleaching recovery techniques, fluorescence-activated cell sorting techniques, etc. Other techniques for determining fluorescence will be known to those of ordinary skill in the art. Thus, as non-limiting examples, a fluorescent detection entity or a fluorescent signaling entity may be detected in a protein solution, a cell lysate, a cell suspension, etc., using spectrofluorimetery techniques, microwell plate readers, or the like, while a fluorescent detection entity or a fluorescent signaling entity may be detected in live and/or intact cells or tissue using fluorescence microscopy, confocal microscopy techniques, etc. As another example, fluorescence-activated cell sorting techniques may be used to sort cells having or expressing a certain amount of oxidized proteins from cells that do not have or express those oxidized proteins. In some cases, samples from multiple subjects may be determined simultaneously, or in rapid succession. For example, in one set of embodiments, a microwell plate reader may be used to determine a plurality of sample from different subjects, for example, in a 96-well plate format, in a 384-well plate format, or the like.

Other examples of techniques that may be useful for determining oxidized proteins include radioactivity detection techniques such as scintillation counters, radioimmunoassay techniques, radiosensitive films, etc. Thus, in one example, cells or tissues containing oxidized proteins that are reacted with a radioactivity detection entity, and/or a detection entity able to interact with a radioactivity signaling entity, may be placed proximate radiosensitive film. The degree of radioactive exposure of the film may be indicative of the concentration of oxidized proteins within the cell or tissue, while the spatial location of the radioactive exposure may be indicative of the spatial distribution of oxidized proteins. Other suitable radioactivity detection techniques will be known to those of ordinary skill in the art.

Still other examples of techniques useful for determining oxidized proteins include detection techniques based on electron densities, for example, electron microscopy, such as TEM or SEM. As an example, a cell or a tissue containing oxidized proteins can be reacted with "heavy" or electron-dense moieties. As used herein, an "electron-dense moiety" is a moiety having an electron density determinably greater than the electron density of the atoms comprising the cell or tissue. Non-limiting examples of electron-dense moieties include gold, osmium, uranium, lead, platinum, chromium, palladium, etc., for example, present as individual atoms (e.g., in a chemical structure), as colloids or microspheres, or the like. A specific non-limiting example is MPB-labeled gold.

In one set of embodiments, binding of the detection entity to the protein is generally non-reversible, i.e., the detection entity may be bound to the protein under relatively benign conditions, but removal of the detection entity from the protein occurs under relatively harsh conditions, and in some cases, the detection entity cannot be removed from the protein without damaging and/or denaturing the protein. One non-limiting example method of determining reversibility is as follows. The detection entity is radiolabeled and reacted with the protein of interest. The unreacted label is removed, and the amount of radioactivity incorporated into the protein is determined, in the presence and in the absence of reducing agent. If the radiolabeled detection entity is reversibly attached, then the amount of radioactivity incorporated into the protein will be different for samples determined in the presence and in the absence of reducing agent; conversely, if the radiolabeled detection entity is non-reversibly attached, then the amount of radioactivity incorporated into the protein will be substantially the same in the presence and in the absence of the reducing agent. Other methods of determining reversibility include using fluorescence, electron-dense moieties, etc.

In yet another aspect, the present invention provides a kit suitable for determining glutathionylated proteins and other oxidized proteins, e.g., in vitro or in vivo, as previously described, optionally including instructions for use of the kit. The kit may include one or more of an alkylating agent, a detection entity, a reducing agent, a signaling entity, antibodies, instructions, suitable containers, or the like. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. As an example, in one embodiment, the kit may include instructions for exposing a sample (e.g., taken from a subject) to a method as described herein for diagnosing the subject as having an oxidative stress condition, e.g., by determining if proteins within the sample have been oxidized and in some cases, to what degree, using the methods as described herein. For instance, the sample may be exposed to an alkylating agent and a reducing agent (such as a glutaredoxin), as described above. As another example, the kit may include instructions for diagnosing an oxidative stress condition in a subject, and prescribing or applying a therapeutic method based on the diagnosis for example, medicine or other therapeutic interventions. The kit may also include other components, depending on the specific application, for example, containers, cell media, salts, buffers, reagents, syringes, needles, etc.

In still another aspect, the invention includes the promotion of one or more of the above-described embodiments. As used herein, "promoted" includes all methods of doing business, including methods of education, scientific inquiry, academic research, industry activity including pharmaceutical industry activity, and any advertising or other promotional activity including written, oral and electronic communication of any form, associated with the invention.

The following applications are incorporated herein by reference: U.S. Provisional Patent Application Ser. No. 60/761,956, filed Jan. 25, 2006, entitled "Detection of Glutathionylated Proteins," by Y. Janssen-Heininger; and U.S. Provisional Patent Application Ser. No. 60/774,060, filed Feb. 16, 2006, entitled "Detection of Glutathionylated Proteins," by Y. Janssen-Heininger.

The following examples are intended to illustrate certain aspects of certain embodiments of the present invention, but do not exemplify the full scope of the invention.

EXAMPLE 1

This example describes certain protocols and methods that may be useful in various embodiments of the invention.

A line of spontaneously transformed mouse alveolar type II epithelial cells (C10) was used in some experiments. The C10 cells were propagated in cell culture media-1066 containing 50 units/ml penicillin and 50 mg/ml streptomycin ("P/S"), 2 mM L-glutamine, and 10% FBS (fetal bovine serum), all from GIBCO/BRL. For experiments involving microscopic analysis, cells were grown on glass coverslips. One hour before exposure to test agents the cells were switched to phenol red free DMEM/F 12, containing 0.5% FBS and P/S.

The primary epithelial cells were isolated from C57BL/6 according to techniques known to those of ordinary skill in the art, with minor modifications. Briefly, trachea were cannulated, filled with MEM media containing 0.1% Protease 14, tied-off and removed from the mouse. After overnight incubation at 4° C. in MEM, the cells were dislodged by opening the ends of the trachea and flushing through 5 ml of MEM containing 10% FBS. The Cells were pelleted and plated on collagen gel coated tissue culture flasks in DMEM/F12 media containing 20 ng/ml cholera toxin, 4 microgram/ml insulin, 5 microgram/ml transferrin, 5 microgram/ml bovine pituitary extract, 10 ng/ml EGF (epidermal growth factor), 100 nM dexamethasone, 2 mM L-glutamine and P/S. For each experiment, the cells were plated on collagen I-coated glass slides. All reagents were purchased from Sigma unless otherwise stated.

Vector construction and transfection was performed using techniques known to those of ordinary skill in the art, as follows. Full length mouse glutaredoxin ("GRX1") was amplified from mouse lung cDNA using PCR with 5'-CATG-GCTCAGGAGTTTGTGA-3' (SEQ ID NO: 1) as the 5'-primer and 5'-GCCACCCCTTTTATAACTGC-3' (SEQ ID NO: 2) as 3'-primer and inserted into TA cloning vector. GRX1 was amplified from this vector using 5'-primer 5'-CCGGATCCATGTACCCATACACGTCCCA-GACTACGCTGCTCAGGAGTTTTGT GAACTG-3' (SEQ ID NO: 3) that introduced a BamHI site, a start codon and HA sequence and as the 3'-primer, 5'-GCCACCCCTTT-TATAACTGCGAATTCCGG-3' (SEQ ID NO: 4), inserting an EcoRI site and a stop codon. The amplified fragment was digested using BamHI and EcoRI and cloned into pcDNA3 expression vector.

Nox and Duox are $H_2O_2$ generating enzymes. Plasmids for Nox1, p41 Nox and p51 Nox were gifts of Dr. David Lambeth, Emory University, Atlanta, Ga. The C10 cells were transfected with 1 microgram HA-GRX1 or pcDNA3 or 0.5 microgram of Nox1 plus 0.5 microgram of p41 Nox plus 0.5 microgram of p51 Nox according to the manufacture's directions (Lipofectamine Plus, Invitrogen) and 24 h after transfection, test agents were added.

Control and GRX1 siRNA (Ambion) were transfected into C10 cells at a concentration of 20 nM using siPORTamine according to the manufacture's directions. At 48 h after transfection, the test agents were added and the experiments performed.

For GRX1 immunocytochemistry, the cells were exposed to test agents, washed twice with PBS (phosphate-buffered saline) and fixed with 4% PFA for 10 min at RT (room temperature, about 25° C.). After three washes with PBS, the cells were permeabilized and blocked simultaneously with PBS containing 0.5% triton and 2% BSA for 10 min at RT. Next, the cells were incubated with rabbit anti-human GRX1 antibody (American Diagnostics), diluted 1:100 in blocking buffer, for 1 h at RT. After three washes with PBS, the cells were incubated for 1 h with goat anti-rabbit Cy-3 in blocking buffer. The nuclei were counterstained with Sytox green (Molecular Probes) for 5 min at RT, the coverslips were mounted and cells analyzed by confocal microscopy using an Olympus BX50 microscope coupled to a Bio-Rad MRC 1024 confocal scanning laser microscope system.

The assessment of GRX catalyzed cysteine derivatization to visualize protein-S-glutathionylation in intact cells was performed as follows. The cells were exposed to test agents, washed twice with PBS and fixed with 4% PFA (paraformaldehyde) for 10 min at RT. After three washes with PBS, cells were permeabilized and free sulfhydryl groups blocked with buffer containing 25 mM Hepes, pH 7.7, 0.1 mM EDTA, 0.01 mM neocuproine, 20 mM N-ethylmaleimide and 0.5% Triton X-100 for 30 min at 4° C. After three washes with PBS, S-glutathionyl mixed disulfides were reduced by incubation with 27 microgram/ml E. coli GRX1 (American Diagnostics), 4 U/ml GSSG reductase (Roche), 1 mM GSH, 1 mM NADPH and 1 mM EDTA in 50 mM Tris, pH 7.5, for 15 min at 37° C.

Next, the cells were washed three times with PBS and newly reduced sulfhydryl groups were labeled with 1 mM N-(3-maleimidylpropionyl)biocytin (MPB, Molecular Probes) for 1 h at RT. After removal of excess MPB by three washes with PBS, cells were incubated with 10 microgram/ml streptavidin-FITC for 1 h at RT and nuclei counter stained with 10 microgram/ml propidium iodide for 30 min at RT. Coverslips were mounted and cells analyzed by confocal microscopy using an Olympus BX50 microscope coupled to a Bio-Rad MRC 1024 confocal scanning laser microscope system. As a negative control, GRX1 alone or GRX1, GSSG reductase, GSH and NADPH were omitted in the reduction step. Furthermore, MPB was omitted in some coverslips to assess the contribution of endogenous biotin.

Western blotting was performed as follows. The cells were lysed in buffer containing 50 mM HEPES, 150 mM NaCl, 1 mM EDTA, 2 mM $MgCl_2$, 10 mM $Na_3VO_4$, 1 mM PMSF, 0.1% NP40, 10 microgram/ml leupeptin, 1% aprotinin, 250 micromolar DTT, 100 micromolar NaF, equalized for protein content and an equal volume of 2× Laemmli sample buffer was added. After boiling the samples for 5 min, proteins were separated on 15% polyacrylamide gels and transferred to nitrocellulose. Following blocking of the membranes overnight in TBS containing 0.05% Tween-20 (TBST) and 5% milk at 4° C., primary antibodies against HA (Upstate) or GRX1 (Labfrontier) were incubated for 4 h at RT. After three 20 min washes with TBST, the membranes were incubated with peroxidase-conjugated secondary antibodies (Jackson ImmunoResearch Laboratories) for 1 h at RT. Conjugated peroxidase was detected by chemiluminescence according to the manufacturer's instructions (Amersham Biosciences).

EXAMPLE 2

Figure 1B:
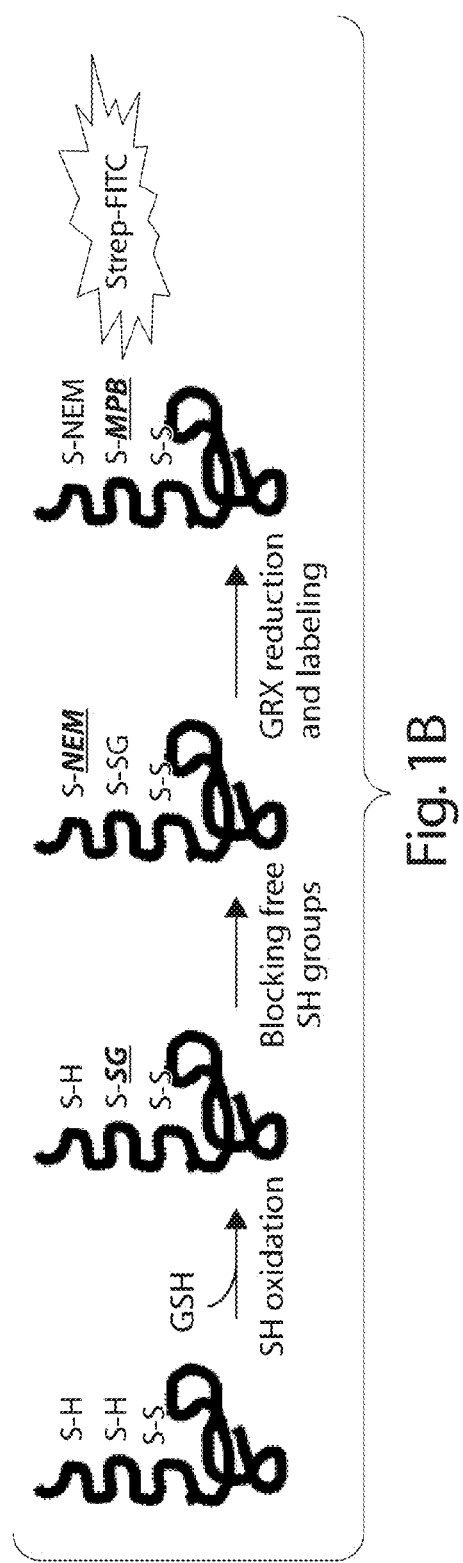
Figure 2A:
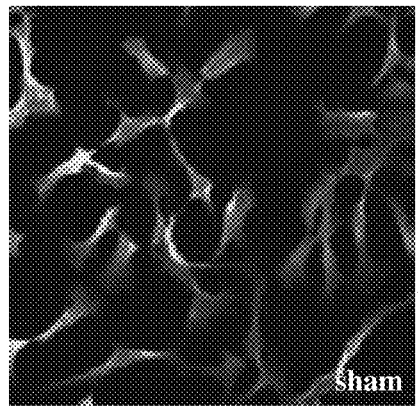
FIGS. 2A-2E are photomicrographs of cells demonstrating the visualization of glutathionylated proteins in cells, according to another embodiment of the invention.
Figure 2B:
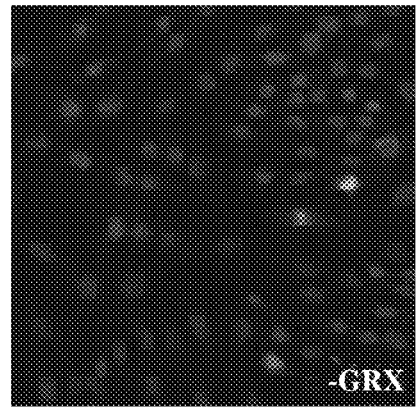
Figure 2C:
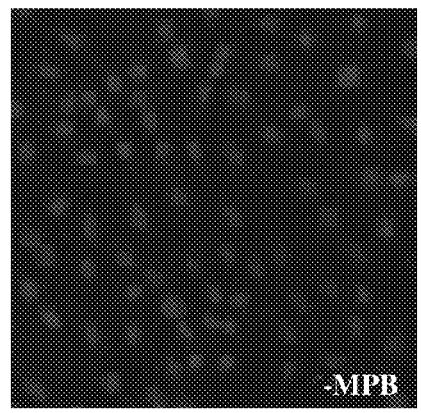
Figure 2D:
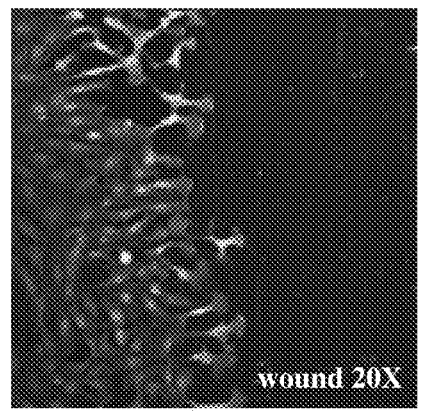
Figure 2E:
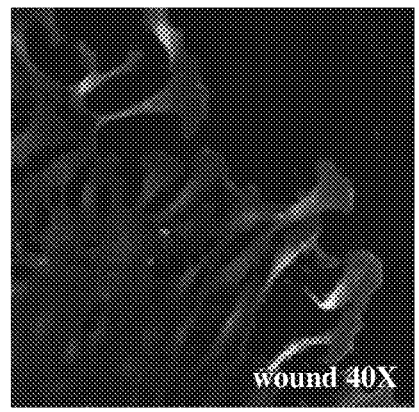

This example illustrates GRX catalyzed cysteine derivatization to visualize protein S-glutathionylation in intact cells. First evaluated was whether GRX-catalyzed reversal of proteins S-glutathionylation could be observed in control cells, according to the protocol depicted in FIG. 1. FIG. 1A illustrates reactions involved in GRX mediated deglutathionylation. In reaction (1), the S-glutathionyl moiety is transferred to GRX. The GRX-S-SG intermediate is reduced by GSH in reaction (2) and GSSG reductase reduces the resulting GSSG using NAPDH in reaction (3). FIG. 1B is a schematic representation of the staining method for GRX reversible cysteine oxidation using in this example. In the first step, free protein thiols are blocked with NEM. In the second step, S-glutathionyl moieties are reduced using GRX1, and next labeled using MPB. Newly biotinylated proteins are then visualized with a detection entity, such as streptavidin-FITC.

FIG. 2 illustrates the visualization of protein S-glutathionylation in intact cells following GRX catalyzed cysteine derivatization. C10 cells were left untreated (FIGS. 2A-2C, 40× objective), or a wound was created using a 1 ml pipet tip on a coverslip of confluent cells and cells were left to recover for 4 h (FIGS. 2D and 2E). GRX reversible cysteine oxidation staining was performed and nuclei were counter stained with propidium iodide. As reagent controls, GRX1 (-GRX, FIG. 2B) or MPB (-MPB, FIG. 2C) were omitted in the staining procedure.

The results in FIG. 2 demonstrate marked MPB-FITC labeling in control cells, which depends on the presence of GRX in the reaction mixture. Furthermore, the omission of MBP resulted in minimal staining, demonstrating that endogenous biotin does not contribute to the observed signal. These reagent controls demonstrated that the labeling method used was specific for GRX-reversible cysteine oxidation, and illustrated that basal protein S-gluathionylation may occur in control cells. It is of interest to note that GRX-catalyzed MPB-FITC labeling was predominant in the cell periphery in association with membrane ruffles, which was particularly noticeable in cells at the leading edge of a wound (FIGS. 2D and 2E).

EXAMPLE 3

This example illustrates increased GRX reversible cysteine oxidation in cells exposed to oxidants. Following these observations, some cells were exposed to certain oxidants that were known to cause the formation of protein glutathione mixed disulfides, and again visualized GRX-reversible cysteine oxidations. Glucose oxidase (GOX), the thiol oxidizing agent diamide, or GSNO were all found to cause a marked increase in GRX catalyzed FITC-MBP labeling (FIGS. 3A-3F). It is of interest to note that the pattern of protein S-glutathionylation after diamide exposure appeared to be highly punctuate in nature, whereas GOX or GSNO caused uniform increases in labeling throughout the cells. Primary epithelial cells isolated from C57BL/6 mice also demonstrated a basal level of glutathione mixed disulfides, which was enhanced after treatment with $H_2O_2$, similar to the C10 cell line.

Figure 3A:
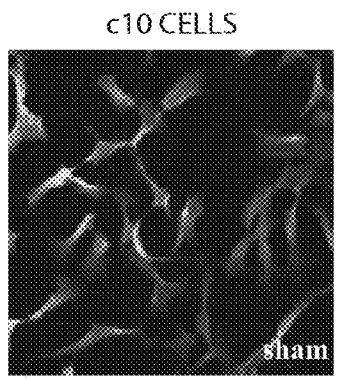
FIGS. 3A-3J are photomicrographs of cells illustrating increased glutaredoxin activity in cells exposed to certain oxidants, in yet another embodiment of the invention.
Figure 3B:
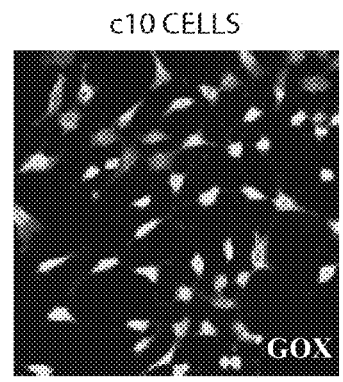
Figure 3C:
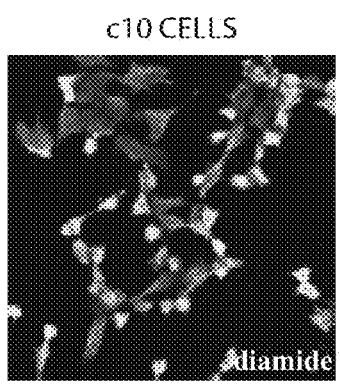
Figure 3D:
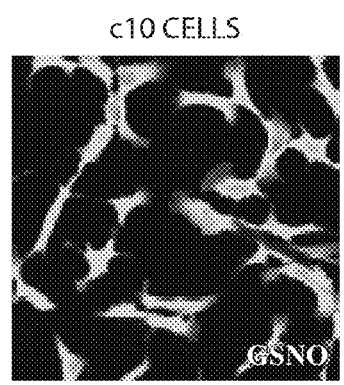
Figure 3E:
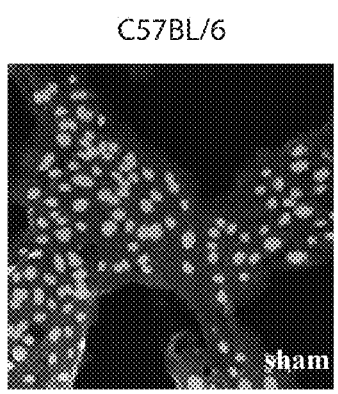
Figure 3F:
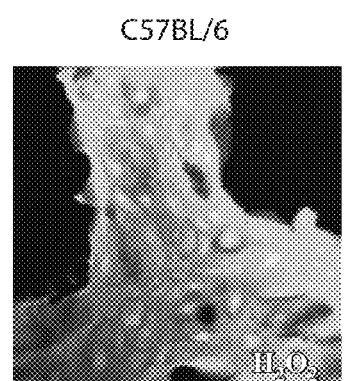
Figure 3G:
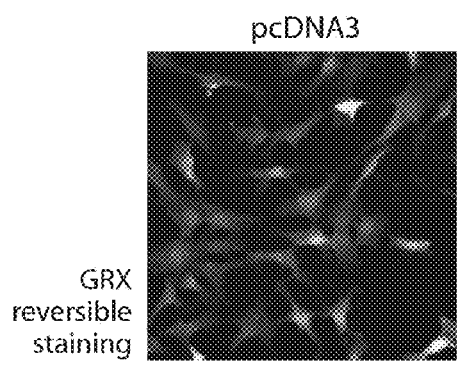
Figure 3H:
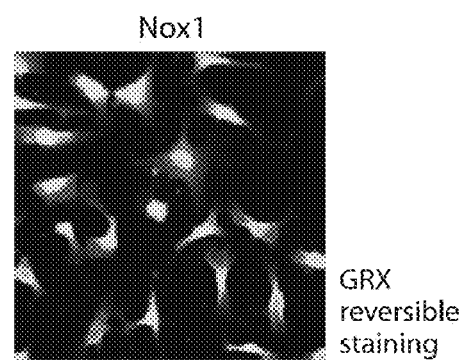

FIGS. 3A-3F illustrate increased GRX reversible cysteine oxidation in cells exposed to oxidants. C10 cells were left untreated or treated with 5 U/ml GOX for 1 h (FIGS. 3A and 3B), 400 micromolar diamide for 15 min, or 1 mM GSNO for 1 h (FIGS. 3C and 3D). Primary tracheal epithelial cells from C57BL/6 mice were left untreated or were exposed to 200 micromolar $H_2O_2$ for 15 min (FIGS. 3E and 3F). GRX reversible cysteine oxidation staining was performed and nuclei were counter stained with propidium iodide (20× objective).

Figure 3I:
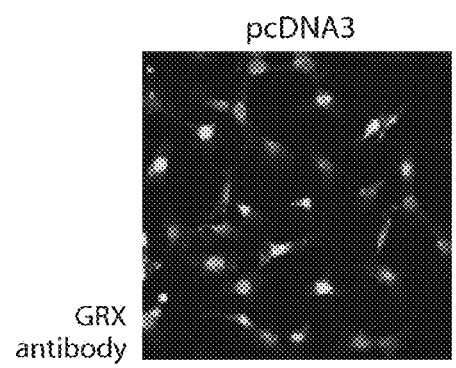
Figure 3J:
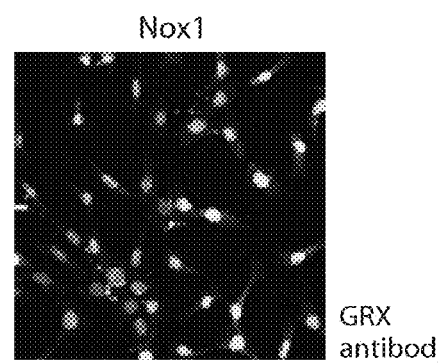
Figure 4A:
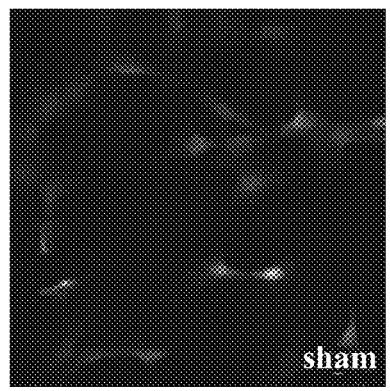
FIGS. 4A-4D are photomicrographs of cells illustrating depletion of glutathione, in still another embodiment of the invention.
Figure 4B:
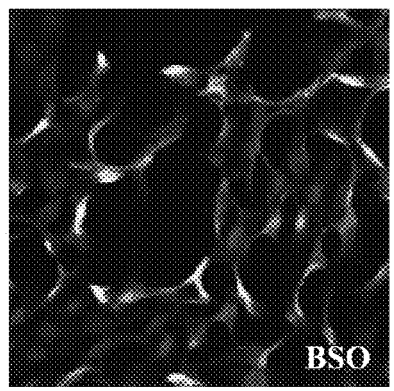
Figure 4C:
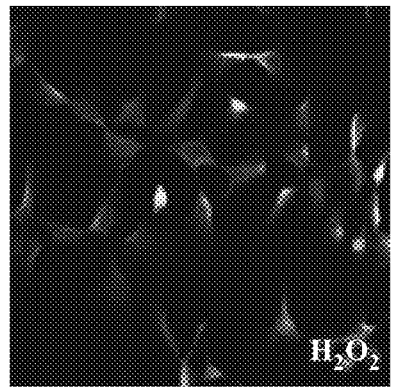
Figure 4D:
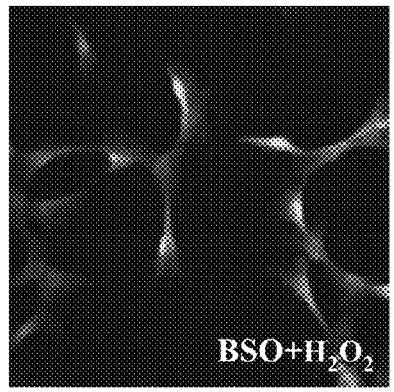

In order to assess the formation of glutathione mixed disulfides in cells that endogenously produce an elevated flux of $H_2O_2$, some cells were transfected with Nox 1 plus its co-activators. Nox1-dependent generation of $H_2O_2$ also resulted in markedly enhanced formation of glutathione mixed disulfides (FIGS. 3G-3J). FIGS. 3G-3J illustrate C10 cells that were transfected with pcDNA3 or Nox1 plus p41 Nox and p51 Nox and stained for GRX reversible cysteine oxidation as in FIGS. 3A-3F. As a control, immunocytochemistry for GRX1 was performed (FIGS. 3I-3J). Nuclei were counter stained with Sytox green (40× objective).

GRX1 expression in cells that overexpress Nox1 plus its co-activators was also assessed, because differences in GRX1 expression could affect the levels of protein-S-glutathionylation (further addressed below). The results illustrated in FIG. 3B suggested that GRX-1 immunoreactivity was not significantly different between pcDNA3 and Nox1 overexpressing cells, illustrating that the differences in S-gluathionylation in Nox1 overexpressing cells were not due to intrinsic differences in GRX1 content.

Quite surprisingly, in resting conditions, or in response to some oxidants, marked staining was revealed at the periphery of cells. Moreover, cells at the leading edge of a wound may display a greater extent of glutathione mixed disulfides, when compared to cells in confluent unwounded areas, which is consistent with enhanced patterns of DCF oxidation at those sites. It is of interest to note that the cell membrane is where the $H_2O_2$ generating enzymes Nox and Duox are localized, which may provide a direct source of oxidants in order to produce S-glutathionylated proteins locally. As the cytoskeleton, and in particular its actin component, may be involved in the formation of membrane ruffles, as well as in migration and cellular plasticity, the actin may represent one of the targets for S-glutathionylation. S-glutathionylation of actin may inhibit its ability to undergo polymerization and form F-actin, and additionally, GRX may be involved in actively mediating actin depolymerization. Thus, dynamic control of actin polymerization/depolymerizaton may represent a key feature in the response of cells to growth factors and other mediators, through its role in the formation of signal transduction scaffolds. These examples thus illustrate a potential role for protein S-glutathionylation in these processes.

EXAMPLE 4

This example illustrates that depletion of glutathione enhances GRX reversible cysteine oxidation. While γ (gamma)-glutamylcysteine synthetase inhibitor, DL-buthionine-[S,R]-sulfoximine (BSO) may deplete the cellular glutathione pool, this agent also may cause increases in levels of glutathione mixed disulfides. In agreement with those previous observations, the results shown in FIGS. 4A-4D demonstrate marked increases in GRX-dependent MPB-FITC labeling in cell treated with BSO, which were most prominent in membrane ruffles, and were further enhanced in cells exposed to $H_2O_2$. In FIGS. 4A-4D, the C10 cells were treated with (1) 0.1 mM BSO for 16 h to deplete glutathione, followed by (2) 200 micromolar $H_2O_2$ for 15 min, as indicated in the lower right corner of each photomicrograph. GRX reversible cysteine oxidation was stained according to the protocol and nuclei were counter stained with propidium iodide (40× objective).

EXAMPLE 5

Figure 5A:
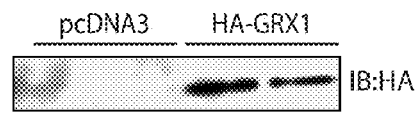
Figure 5B:
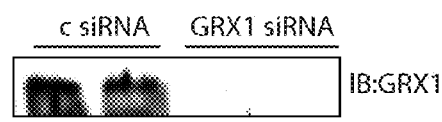
Figure 5C:
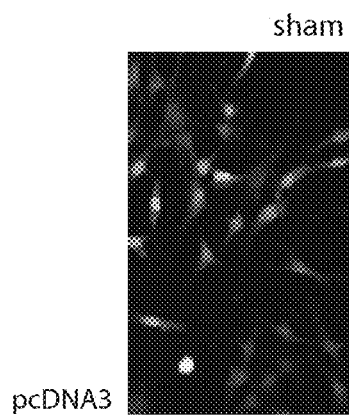
Figure 5D:
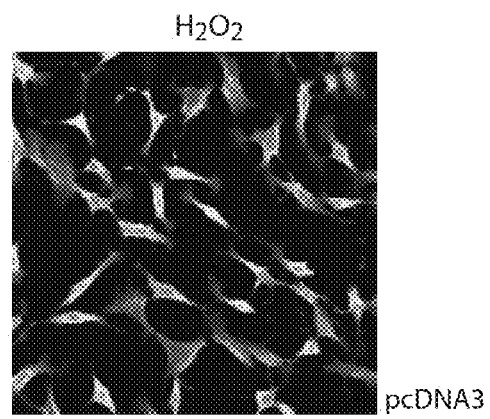
Figure 5E:
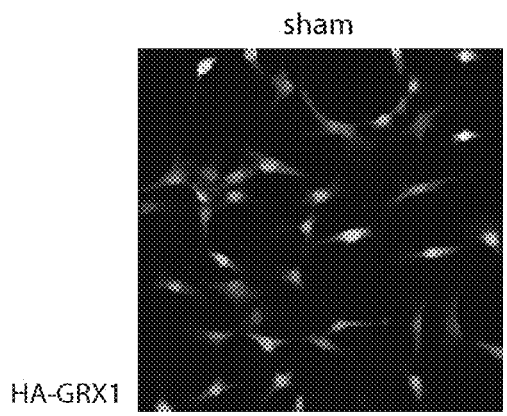
Figure 5F:
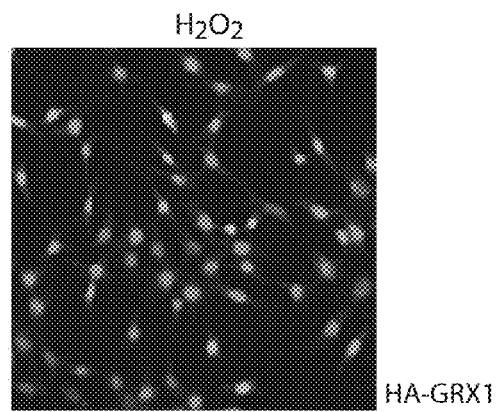

This example illustrates that manipulation of cellular GRX1 affects levels of S-glutathionylated proteins detected in situ. Since GRX1 specifically reverses protein-glutathione mixed disulfides next GRX1 expression was manipulated in some cells, in order to augment or attenuate S-glutathionylation, to show that the labeling approach used so far indeed detects S-glutathionylated proteins. Referring now to FIG. 5, C10 cells were transfected with pcDNA3, HA-GRX1 (FIGS. 5A and 5C-5F), control siRNA (c siRNA) or GRX1 siRNA (FIGS. 5B and 5G-5J). FIGS. 5A and 5B are Western blots for HA or GRX1. FIGS. 5C-5J illustrate cells left untreated or treated with 200 micromolar $H_2O_2$ for 15 min and stained for GRX reversible cysteine oxidation. Nuclei were counter stained with propidium iodide (40+ objective).

First, transfected C10 cells with HA-GRX1 were used, which was confirmed by Western blot for HA (FIG. 5A). Whereas overexpression of GRX1 in C10 cells did not appear to attenuate the basal level of cellular glutathione mixed disulfides (FIGS. 5C-5F), GRX1 overexpression generally prevented the increased formation of S-glutathionylated proteins in response to $H_2O_2$, seen in pcDNA3 transfected cells.

Lastly, RNA interference to selectively inhibit the expression of GRX 1 resulted in significantly decreases in protein expression of GRX1 (FIG. 5B). Importantly, knock-down of GRX1 was sufficient to enhance basal cellular S-glutathionylation, and substantially increased the formation of S-glutathionylated proteins in response to $H_2O_2$ (FIGS. 5G-5J).

Collectively, these findings demonstrate that the patterns of FITC-MBP labeling observed in the presence of catalytically active GRX1 may be due to protein-S-glutathionylation, and that the staining patterns may change substantially in a cell under conditions of oxidative stress or following manipulation of endogenous GRX1.

Thus, various oxidants, including bolus $H_2O_2$, diamide, GSNO, GOX, and $H_2O_2$ production through overexpression of Nox1 all led to enhanced staining for S-glutathionylated proteins. However, the staining patterns that these various oxidants and oxidant generating systems inflicted displayed marked differences. Nox1 overexpression appeared not to have altered GRX1 protein levels. The observation that S-glutathionylation is enhanced in cells under glutathione depleted conditions was surprising. However, as GSH may be an essential cofactor for GRX catalyzed deglutathionylation, depletion of GSH could limit the extent of GRX activity, resulting in enhanced S-glutathionylation. On the other hand, if S-glutathionylation represents a mechanism that protects protein thiols from irreversible oxidation, the available GSH may become conjugated to protein thiols in a pro-oxidative environment of low GSH levels.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for determining a glutathionylated protein, comprising:
   reacting a first thiol moiety on a protein to form an alkylthio moiety;
   reacting a glutathionylated moiety on the protein to form a second thiol moiety; and
   reacting the second thiol moiety with an alkylating agent comprising a detection entity to form a second alkylthio moiety to determine protein glutathionylation.

2. The method of claim 1, wherein the protein is in a tissue.

3. The method of claim 2, further comprising determining the location of the protein using fluorescence of the detection entity within the tissue.

4. The method of claim 1, wherein the step of reacting a first thiol moiety comprises reacting the first thiol moiety with N-ethylmaleimide to form the alkylthio moiety.

5. The method of claim 1, wherein the step of reacting a glutathionylated moiety comprises reacting a glutathionylated moiety with a reductase to form the second thiol moiety.

6. The method of claim 5, wherein the step of reacting a glutathionylated moiety comprises reacting a glutathionylated moiety with a glutaredoxin.

7. The method of claim 1, wherein the step of reacting the second thiol moiety comprises reacting the second thiol moiety with N-(3-maleimidylpropionyl)biocytin to form the second alkylthio moiety.

* * * * *